United States Patent
Muller (10) Patent No.: US 10,824,892 B2
(45) Date of Patent: Nov. 3, 2020

(54) SYSTEM AND METHOD FOR IMAGING AN OBJECT VIA PRE-SHOT PROCESSING

(71) Applicant: GENERAL ELECTRIC COMPANY, Schenectady, NY (US)

(72) Inventor: Serge Louis Wilfrid Muller, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 82 days.

(21) Appl. No.: 16/024,518

(22) Filed: Jun. 29, 2018

(65) Prior Publication Data

US 2020/0005064 A1 Jan. 2, 2020

(51) Int. Cl.
*G06K 9/03* (2006.01)
*G06T 7/00* (2017.01)

(52) U.S. Cl.
CPC .............. *G06K 9/03* (2013.01); *G06T 7/0012* (2013.01); *G06T 2207/10116* (2013.01); *G06T 2207/20084* (2013.01); *G06T 2207/30068* (2013.01)

(58) Field of Classification Search
CPC ......... G06T 7/0012; G06T 2207/10088; G06T 2207/10064; G06T 2207/10081; G06T 2207/10116; G06T 2207/20081; G06T 2207/30004; G06T 2207/30016; G06T 2207/30068; G06T 2207/30096; G06T 7/62; G06T 11/006; G06T 11/008; G06T 2200/24; G06T 2207/10056; G06K 9/00147; G06K 9/627; G06K 2209/051; G06K 9/6223; G06K 9/66; G06K 2009/4695; G06K 2209/05; G06K 9/00134; G06K 9/03; G06K 9/3233; G06K 9/40; G06K 9/4604; G06K 9/4628; G06K 9/527; G06K 9/6227; G06K 9/6232; G06K 9/6247; G06K 9/6249; G06K 9/6255
See application file for complete search history.

(56) References Cited

U.S. PATENT DOCUMENTS 6,827,489 B2 12/2004 Nicolas et al.
2009/0279672 A1 11/2009 Reiner
(Continued)

FOREIGN PATENT DOCUMENTS

| WO | 2012080914 A1 | 6/2012 | |
|----|---|---|---|
| WO | 2018015911 A1 | 1/2018 | |
| WO | 2018-65812 M * | 8/2018 | ............... A61B 5/00 |

OTHER PUBLICATIONS

Aurelie D. Laidevant, et al; "Compositional Breast Imaging Using a Dual-Energy Mammography Protocol" Med. Phys. vol. 37, No. 1; Jan. 2010.
(Continued)

*Primary Examiner* — Golam Sorowar
(74) *Attorney, Agent, or Firm* — Grogan, Tuccillo & Vanderleeden, LLP (57) ABSTRACT

A system for imaging an object via pre-shot processing is provided. The system includes an imaging device operative to image the object, and a controller in electronic communication with the imaging device. The controller is operative to acquire at least one pre-shot image of the object via the imaging device; and to generate, based at least in part on the at least one pre-shot image, an indicator that corresponds to a likelihood that one or more diagnostic images of the object acquired via the imaging device will be medically deficient.

19 Claims, 6 Drawing Sheets

(56) References Cited

U.S. PATENT DOCUMENTS

| | | |
|---|---|---|
| 2013/0121556 A1 | 5/2013 | Matsumoto |
| 2013/0251104 A1 | 9/2013 | Roessl |
| 2015/0199478 A1 | 7/2015 | Bhatia |
| 2016/0189376 A1* | 6/2016 | Bernard ............... G06T 11/006 382/132 |
| 2016/0364862 A1* | 12/2016 | Reicher ............... A61B 5/7267 |
| 2017/0014108 A1* | 1/2017 | Mazurowski ...... A61B 10/0041 |

OTHER PUBLICATIONS

European patent application 19183103.1 filed Jun. 28, 2019; European Search Report dated Dec. 12, 2019; 7 pages.

* cited by examiner

SYSTEM AND METHOD FOR IMAGING AN OBJECT VIA PRE-SHOT PROCESSING

BACKGROUND

Technical Field

Embodiments of the invention relate generally to medical imaging, and more specifically, to systems and methods for imaging an object via pre-shot processing.

Discussion of Art

X-ray diagnostic imaging is often used to image internal structures of a patient. Many x-ray based imaging systems obtain images by directing x-rays through the tissues of a patient via an x-ray emitter/tube. In such systems, a body part of interest is placed between the emitter and a detector such that some of the emitted x-rays pass through the body part and strike the detector so as to generate a projection of internal structures within the body part. As will be understood, some of the x-rays that are directed through the body part are absorbed by the tissues. Thus, it is generally desirable to reduce the amount of x-rays a patient is exposed to.

In many x-ray based imaging systems, a radiologist/technologist is able to determine if acquired diagnostic images are acceptable, e.g., sufficient for medical diagnostic purposes, only after such images have been obtained. As will be appreciated, however, numerous issues may render a diagnostic image unacceptable, i.e., insufficient for medical diagnostic purposes, which in turn, may require obtaining additional diagnostics images, thereby increasing the patient's amount of x-ray exposure. For example, the body part intended to be imaged may be partially outside the field of view ("FOV") of the imaging system and/or otherwise disposed in a position not suitable for medical diagnostic purposes.

As will be understood, the quality of an x-ray image is typically based in part on the amount of x-rays used to generate the image. Typically, the higher the amount of x-rays used to obtain an image, the higher the quality and the more likely the image will be acceptable for medical diagnostic purposes. Accordingly, some x-ray based imaging systems seek to predict/improve the acceptability of a diagnostic image by taking an initial image of a body part of interest using a lower amount of x-rays than the amounts typically used to generate acceptable diagnostic images. In other words, some x-ray based imaging systems obtain an initial image that, while potentially unsuitable for medical diagnostic purposes, is suitable for detecting positioning issues with respect to a body part of interest that may render subsequent diagnostics images unacceptable.

As will be appreciated, however, such x-ray based imaging systems typically require manual inspection of the initial image by a technician/radiologist, and are usually capable of detecting only major positioning issues, e.g., scenarios where a large part of the body part of interest is outside the FOV of the imaging system. Accordingly, such x-ray based imaging systems may fail to detect positioning issues where the body part of interest is properly contained within the FOV, but where one or more internal structures within the body part are misaligned. Additionally, such x-ray based imaging systems may be incapable of determining whether an internal structure simply cannot, or should not, be imaged due to various non-positional related issues, e.g., masking/obscuring/hiding of a lesion by healthy tissue, blocking/absorption of x-rays due to highly dense tissues, etc.

What is needed, therefore, is an improved system and method for imaging an object via pre-shot processing.

BRIEF DESCRIPTION

In an embodiment, a system for imaging an object via pre-shot processing is provided. The system includes an imaging device operative to image the object, and a controller in electronic communication with the imaging device. The controller is operative to acquire at least one pre-shot image of the object via the imaging device; and to generate, based at least in part on the at least one pre-shot image, an indicator that corresponds to a likelihood that one or more diagnostic images of the object acquired via the imaging device will be medically deficient.

In another embodiment, a method for imaging an object via pre-shot processing is provided. The method includes acquiring at least one pre-shot image of the object via an imaging device. The method further includes generating, via a controller and based at least in part on the at least one pre-shot image, an indicator that corresponds to a likelihood that one or more diagnostic images of the object acquired via the imaging device will be medically deficient.

In yet another embodiment, a non-transitory computer readable medium storing instructions is provided. The stored instructions adapt a controller to acquire at least one pre-shot image of an object via an imaging device. The stored instructions further adapt the controller to generate, based at least in part on the at least one pre-shot image, an indicator that corresponds to a likelihood that one or more diagnostic images of the object acquired via the imaging device will be medically deficient.

In yet another embodiment, a system for imaging an object via pre-shot processing is provided. The system includes an imaging device operative to image the object, and a controller in electronic communication with the imaging device. The controller is operative to acquire the at least one pre-shot image using a first energy spectrum, and to acquire one or more diagnostic images via the imaging device using a second energy spectrum lower than the first energy spectrum. The controller is further operative to generate a material-equivalent image based at least in part on the at least one pre-shot image and the one or more diagnostic images.

In yet another embodiment, a non-transitory computer readable medium storing instructions is provided. The stored instructions adapt a controller to acquire at least one pre-shot image via an imaging device using a first energy spectrum; and to acquire one or more diagnostic images via the imaging device using a second energy spectrum lower than the first energy spectrum. The stored instructions further adapt the controller to generate a material-equivalent image based at least in part on the at least one pre-shot image and the one or more diagnostic images.

DRAWINGS

The present invention will be better understood from reading the following description of non-limiting embodiments, with reference to the attached drawings, wherein below.

DETAILED DESCRIPTION

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

As used herein with respect to images and/or the acquisition of images, the term "pre-shot" refers to an image that is acquired/obtained via an electromagnetic radiation based imaging system, e.g., an x-ray imaging system, prior to the acquisition of diagnostic images by the system at an amount of radiation lower than that generally used by the system to acquire/obtain the diagnostic images. The term "diagnostic image", as used herein, refers to images acquired/obtained via an electromagnetic radiation based imaging system typically, but not always, on the order of ten-times (10×) the amount of radiation of a pre-shot image acquired by the same imaging system. The term "medically deficient", as used herein with respect to diagnostic images, means that the diagnostic images are/or would be substantially unacceptable for use in making a medical diagnosis, or otherwise constitute an unnecessary, detrimental, and/or avoidable radiation exposure to a patient, i.e., diagnostic images that should not be, or should not have been, acquired. The term "pre-shot processing", as used herein, means to process and/or analyze a pre-shot image. As used herein, the term "material-equivalent image" refers to a constructed image based at least in part on combining two or more images each acquired with a different electromagnetic spectrum, e.g., x-ray spectra, wherein the constructed image depicts the thickness and/or amount of one or more types of materials, e.g., water, fats, bone, protein, etc., within an object. Accordingly, the terms "water image" and "water-equivalent image" refer to a type of material-equivalent image that depicts the thickness and/or amount of water within an object; the terms "fat image" and "fat-equivalent image" refer to a type of material-equivalent image that depicts the thickness and/or amount of fat within an object; and the terms "protein image" and "protein-equivalent image" refer to a type of material-equivalent image that depicts the thickness and/or amount of protein within an object.

Further, while the embodiments disclosed herein are described with respect to a mammography imaging system and procedure, it is to be understood that embodiments of the present invention may be applicable to other types of medical imaging systems and/or procedures that involve radiating a patient/subject/object, e.g., chest x-rays. Further still, as will be appreciated, embodiments of the present invention related imaging systems may be used to analyze tissue generally and are not limited to human tissue.

Figure 1:
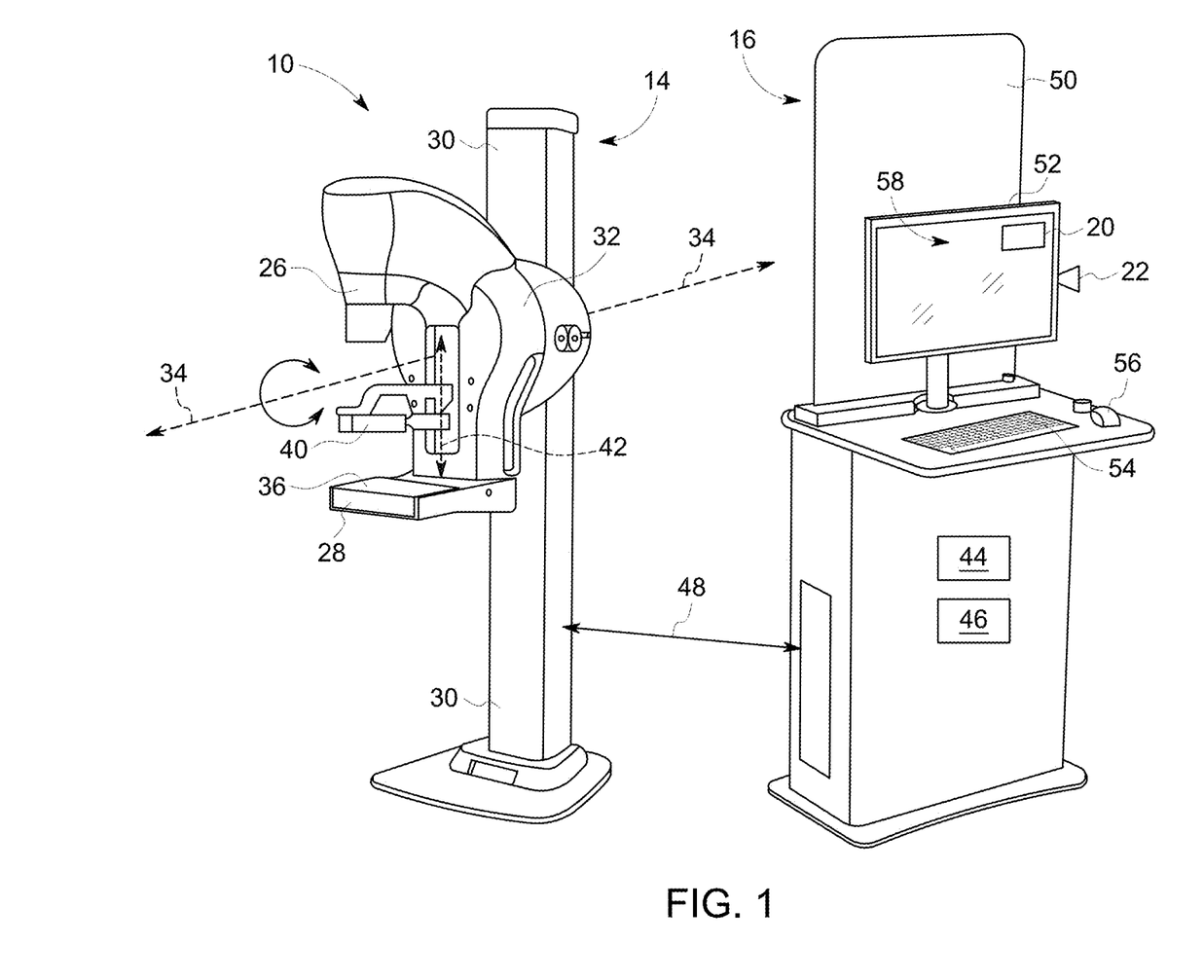
FIG. 1 is a perspective view of a system for imaging an object via pre-shot processing, in accordance with an embodiment of the present invention.

Referring now to FIG. 1, the major components of a system 10 for imaging an object (12 FIG. 3) via pre-shot processing, in accordance with an embodiment of the present invention, is shown. The system 10 includes an imaging device/system 14 and a controller 16. The imaging device 14 is operative to image the object 12, e.g., a human breast or other body part. The controller 16 electronically communicates with the imaging device 14 and is operative to acquire at least one pre-shot image 18 (FIG. 3) of the object 12 via the imaging device 14. As will be explained in greater detail below, the controller 16 is further operative to generate, based at least in part on the at least one pre-shot image 18, an indicator 20, 22 that corresponds to a likelihood that one or more diagnostic images of the object 12 acquired 24 (FIG. 2) via the imaging device 14 will be medically deficient.

Figure 3:
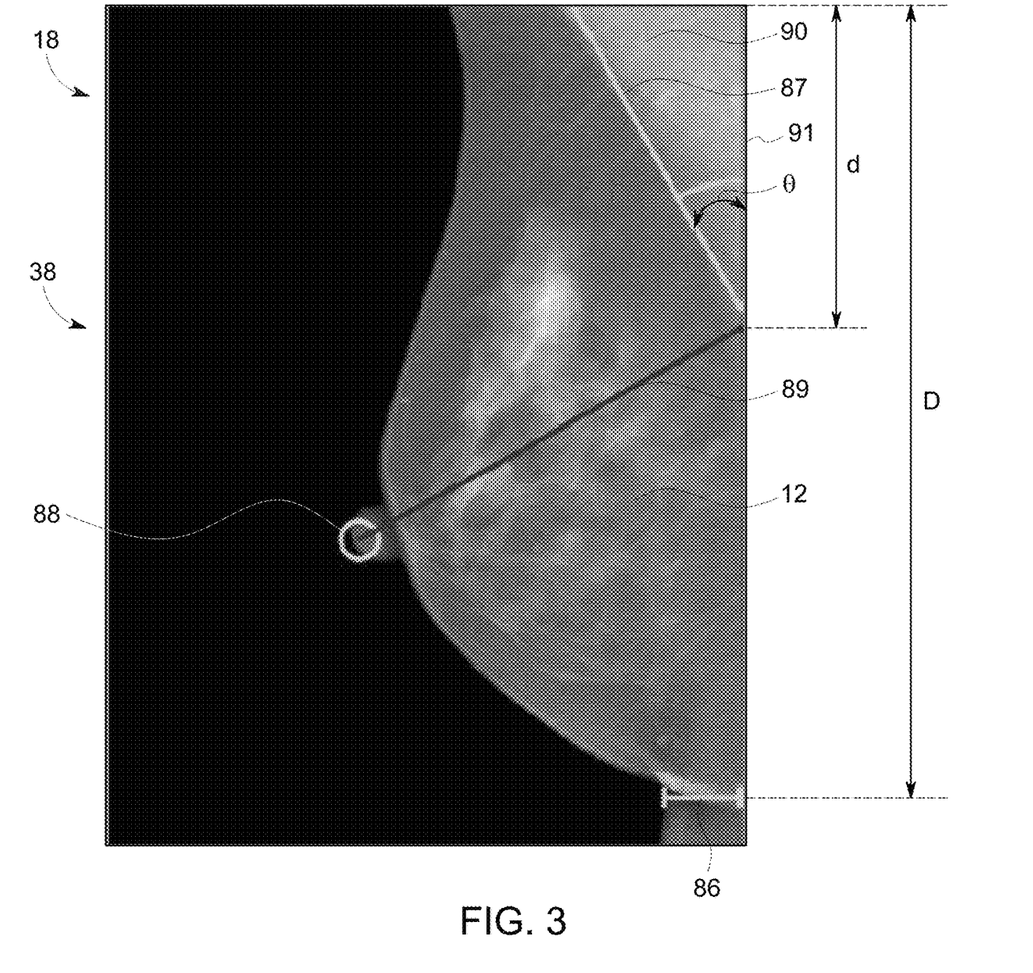
FIG. 3 is a diagram of a pre-shot image of an object taken by the system of FIG. 1, in accordance with an embodiment of the present invention.

Accordingly, as shown in FIG. 1, the imaging device 14 includes a radiation source/emitter 26 and a radiation detector 28. The radiation source 26 is operative to emit radiation rays and, in embodiments, is selectively adjustable between one or more positions, e.g., the radiation source 26 may be mounted to a stand/support 30 via a rotatable mount 32 such that the radiation source 26 rotates about a longitudinal axis 34. The radiation detector 28 is operative to receive the radiation rays and has a surface 36 that defines an imaging region 38 (FIG. 3). In embodiments, the imaging device 14 may include one or more paddles 40, e.g., a compression plate, mounted to the stand 30 and slidably adjustable along axis 42 (and/or other axis/direction) so as to compress and/or restrain the object 12 against the surface 36. In embodiments, the imaging device 14 may form part of/be a mammography device.

In embodiments, the controller 16 may be a workstation having at least one processor 44 and a memory device 46. In other embodiments, the controller 16 may be embedded/integrated into one or more of the various components of the system 10 disclosed above. In embodiments, the controller 16 may be in electrical communication with the radiation source 26, radiation detector 28, the paddles 40, and/or other components of the system 10 via a datalink/connection 48. As will be appreciated, in embodiments, the datalink 48 may be a wired and/or wireless connection. In embodiments, the controller 16 may include a radiation shield 50 that protects an operator of the system 10 from the radiation rays emitted by the radiation source 26. The controller 16 may further include a display 52, a keyboard 54, mouse 56, and/or other appropriate user input devices, that facilitate control of the system 10 via a user interface 58.

Figure 2:
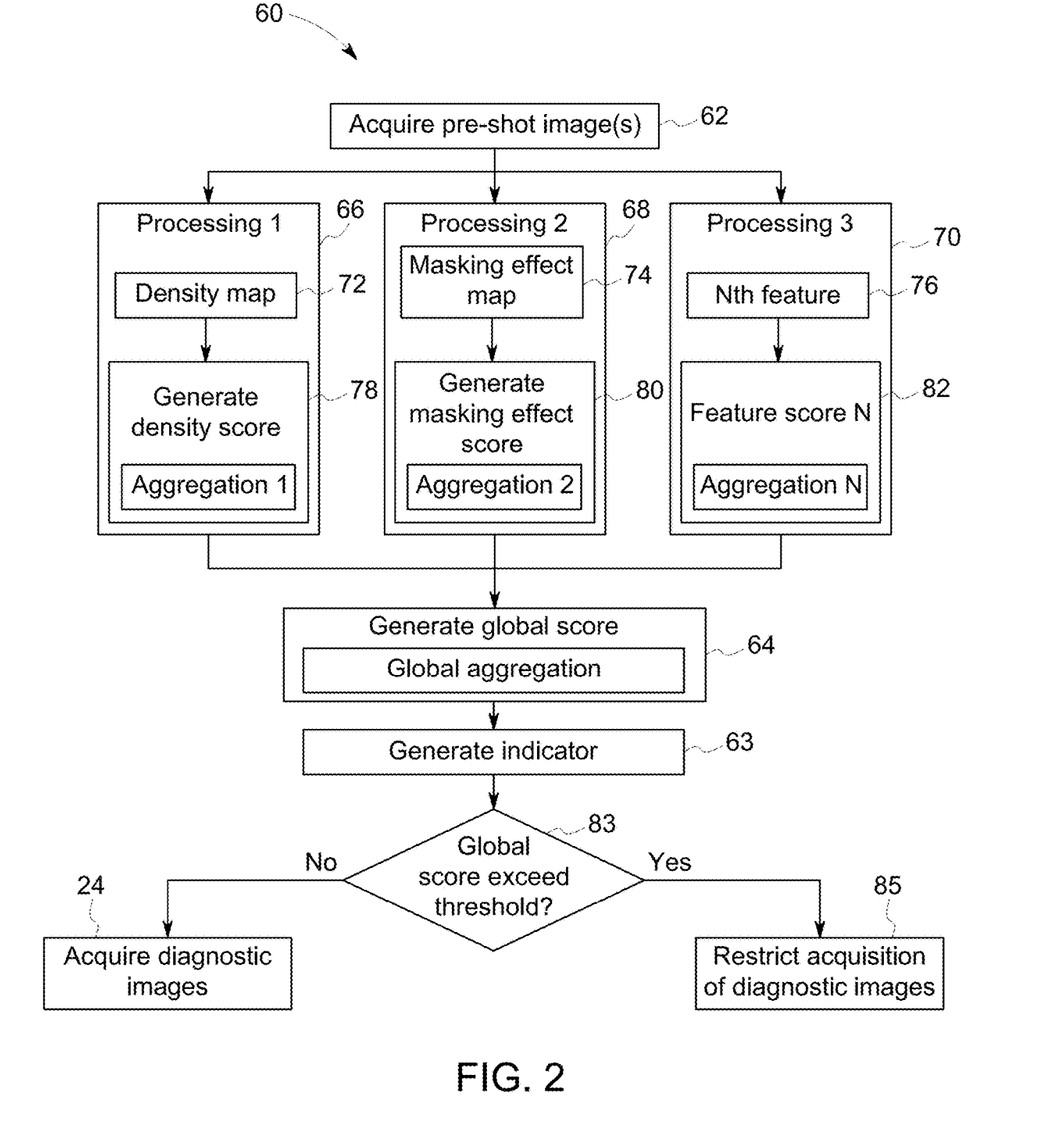
FIG. 2 is a flow chart of a method for imaging an object via pre-shot processing utilizing the system of FIG. 1, in accordance with an embodiment of the present invention.

Illustrated in FIG. 2 is a flow chart depicting a method 60 for imaging an object 12 (FIG. 3) via pre-shot processing utilizing the system 10 (FIG. 1), in accordance with an embodiment of the present invention. As discussed above, the method 60 includes acquiring 62 the at least one pre-shot image 18 via the imaging device 14, and generating 63 the indicator 20, 22 based at least in part on the at least one pre-shot image 18. In embodiments, the indicator may be a visual indicator 20, e.g., an on-screen message box, light, etc., and/or audio indicator 22, e.g., a chime, beep, machine simulated voice, .wav file, etc.

In embodiments, the method 60 may further include generating 64 a global score derived from one or more features/qualities/characteristics of the at least one pre-shot image 18, e.g., object 12 density, object 12 masking effect, object 12 position, and/or other suitable qualities/features/characteristics of the pre-shot image 18 and/or the object 12. In such embodiments, indicators 20, 22 may be generated 63 based at least in part on the global score.

The method 60 may have processing paths 66, 68, 70 for each of the one or more features, wherein each processing path acquires/generates 72, 74, 76 a map of the respective feature, and then generates 78, 80, 82 a component/sub-score used to generate 64 the global score. As used herein, the terms "map" and "feature map" refer to a mapping of a quantity/degree of a characteristic/feature/quality of the pre-shot images 18. For example, a density mapping may depict the density of a body part in a pre-shot image via gray scale in which the lighter a pixel is the more dense the corresponding region of the object is, e.g., a map depicting/conveying the relative or absolute quantity and/or location of fibroglandular tissue in the breast. As will be understood, the global score 64 may correspond to a risk that the object/patient 12 may have a cancer that will not be depicted through/in the x-ray diagnostic images.

Accordingly, in embodiments, the one or more processing paths 66, 68, 70 may respectively correspond to density of the object 12, e.g., path 66, masking effect of the object 12, e.g., path 68, and additional appropriate features, e.g., path 70 representative of the Nth feature. As used herein, the term "masking effect" refers to the likelihood that a particular region of the object 12 is obscuring a sub-object/region of interest, e.g., a lesion. For example, a highly heterogeneous content of normal tissues in the breast may have a high masking effect due to their tendency to obscure/hide tumors within the tissues of a breast.

In embodiments, the method 60 may further include determining 83 whether the global score exceeds a threshold, and restricting 85 subsequent acquisition 24 of the diagnostic images if the threshold is exceeded. For example, in embodiments, the global score may be on a scale of zero (0) to one-hundred (100), with zero (0) representing the lowest likelihood that the acquired 24 diagnostic images will be medically deficient, and with one-hundred (100) representing the highest likelihood that the acquired 24 diagnostic images will be medically deficient. In such embodiments, the threshold 83 may be about ten percent (10%), e.g., the controller 16 will prevent/restrict 85 acquisition 24 of the diagnostic images when analysis/processing 66, 68, 70 of the feature/maps 72, 74, 76 indicates a ten percent (10%) chance that the acquired 24 diagnostic images would be medically deficient.

Turning now to FIG. 3, in embodiments, one of the features, e.g., the Nth feature 76 (FIG. 3), may be a position of the object 12. For example, as shown in FIG. 3, the object 12 may be a human breast with the corresponding feature score 82 (FIG. 2) based at least in part on one of: an inframammary fold 86 of the breast 12, a nipple 88 of the breast 12, and/or a pectoral muscle 90 associated with the breast 12. For example, the controller 16 may determine if the breast 12 is in a proper position by analyzing one or more geometrical features formed by the structures of the breast 12, e.g., the ratio of d/D where D is the distance from about the inframammary fold 86 to about the top of the image 18 and d is the distance from about the top of the image 18 to about the intersection of the edge 91 of the image 18 with a line 89 substantially perpendicular to the edge 87 of the pectoral muscle 90 and passing through the nipple 88. In embodiments, the geometrical fractures may include the angle θ formed between the edge 91 of the imaging region 38, closest to the edge 87 of the pectoral muscle 90, and/or the edge 87 of the pectoral muscle 90 itself. In embodiments, other relationships/properties of the breast/object 12 may be used to generate the positional feature score 82, e.g., the amount and/or shape of tissue detected below the inframammary fold 86.

As also discussed above, many errors in medical diagnostic imaging are human errors that result in imaging of the incorrect/wrong body part. For example, an operator of an imaging system may image a right breast when imaging of the left breast was intended/desired. Thus, as will be appreciated, embodiments of the present invention seek to reduce/mitigate and/or eliminate such errors, and in turn, reduce unnecessary radiation exposure to a patient by verifying that the body part 12 in the pre-shot image 18 is the desired/expected body part to be imaged prior to acquiring 24 diagnostic images of the body part 12.

Accordingly, in embodiments, one feature, e.g., the Nth feature 76 (FIG. 3), which may contribute to, or be independent from, positional analysis/mapping is matching of an anatomical symmetry, i.e., laterality, to the object 12, e.g., determining that the object 12 is a left medio-lateral oblique image or a right cranio-caudal image of a breast. In embodiments, the controller 12 may determine the anatomical symmetry/laterality and/or position of the breast 12 based at least in part on the position of the pectoral muscle 90, glandular tissue distribution, the nipple 88, contour of the skin, and/or other structures/relationships discernable in the pre-shot image 18. For example, the controller 12 may detect that, in combination with information/data provided by the imaging device 14, e.g., rotation angle as measured at the rotatable mount 32 (FIG. 1), the shape of the edge 87 of the pectoral muscle 90 and/or the quantity of tissue below the inframammary fold 86 corresponds with a left or a right breast.

In such embodiments, the controller 16 may restrict 85 (FIG. 2) acquisition 24 of diagnostic images when the matched anatomical symmetry of the object 12 does not match an expected anatomical symmetry of the object 12. In other words, if the controller 16, based on user input, expects to see/detect a left breast in the pre-shot image 18, but instead sees/detects a right breast, the controller 16 may prevent/restrict 85 the subsequent acquisition 24 of the diagnostic images.

Figure 4:
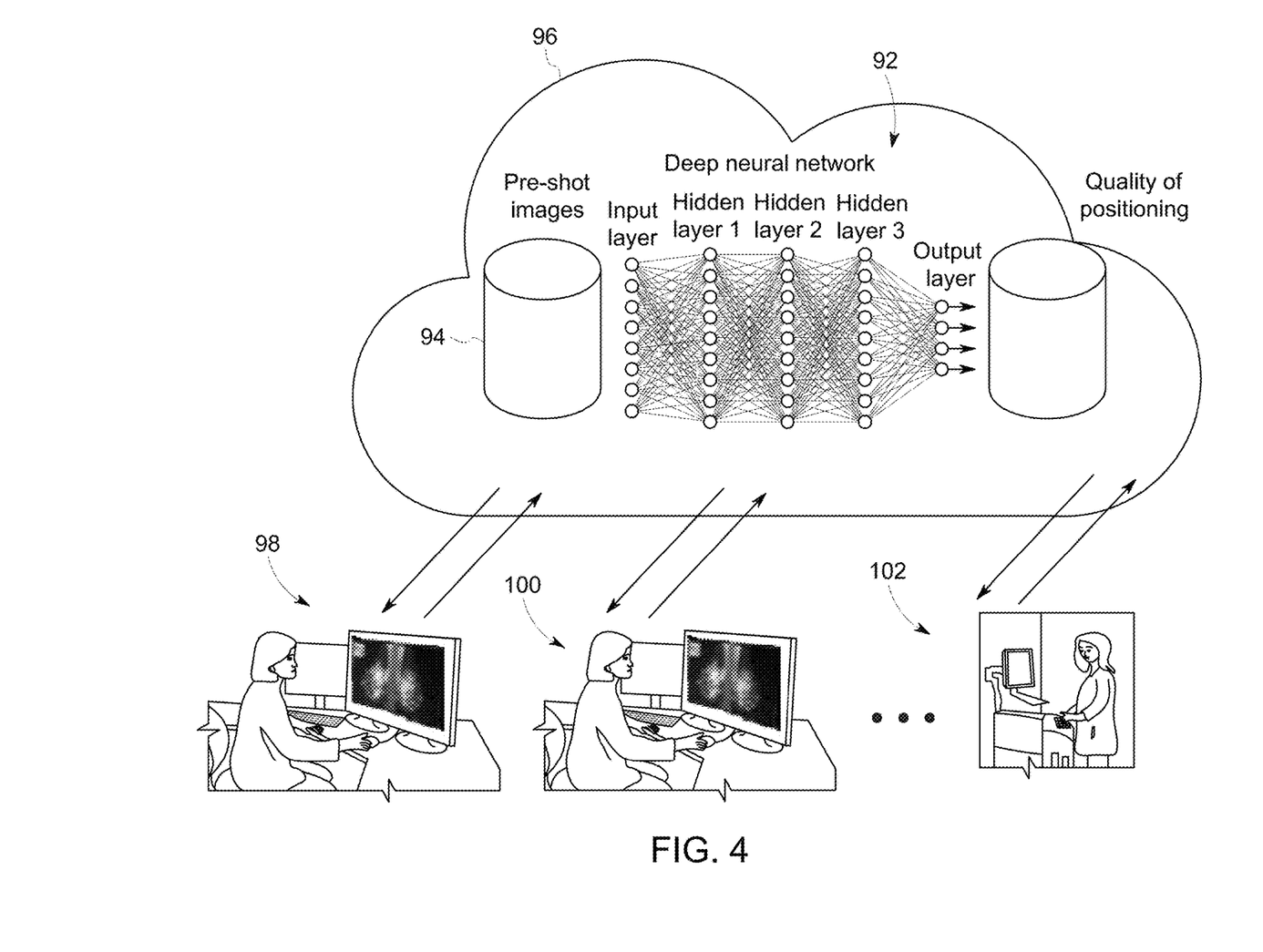
FIG. 4 is a diagram of a machine learning model of the system of FIG. 1, in accordance with an embodiment of the present invention.

Referring now to FIG. 4, in embodiments, the controller 16 may generate the indicator 20, 22 based at least in part on a machine learning model 92, e.g., an artificial neural network, i.e., artificial intelligence may be used as opposed to a more standard defined sets of rules. As such, a plurality of pre-shot images acquired from various objects/patients may be stored in a database 94. In embodiments, a cloud 96 architecture, e.g., a computer network, may be implemented to enable one or more experts 98, 100, 102, e.g., medical doctors and/or technologists, to assign global scores to each of the pre-shot images in the database 94 so as to form a paired training set.

The machine learning model 92 may then be trained in a supervised manner with the pre-shot image/global score pairs to generate a global score for any given pre-shot image. In other words, in embodiments, the machine learning model 92 may be trained to discriminate good from poor patient and/or organ positioning in a pre-shot image, or to otherwise determine that the diagnostic images 24 should not be acquired until the object 12 is repositioned, or not acquired at all. For example, in embodiments, the machine learning model 92, or the controller 16 using results generated from the machine learning model 92, may determine from a pre-shot image 18 that subsequent image acquisition may lead to diagnostic images that would be medically deficient. In embodiments, the global score generated by the machine learning model 92 may be on a discrete scale, e.g., unacceptable, poor, fair, good, and/or excellent; or, in other embodiments, on a continuous scale, e.g., zero percent (0%) to one-hundred percent (100%). Additionally, while the above discussion concerns training the machine learning model 92 with pre-shot images, it will be understood that embodiments of the present invention may train the machine learning model 92 on diagnostic images.

Figure 5:
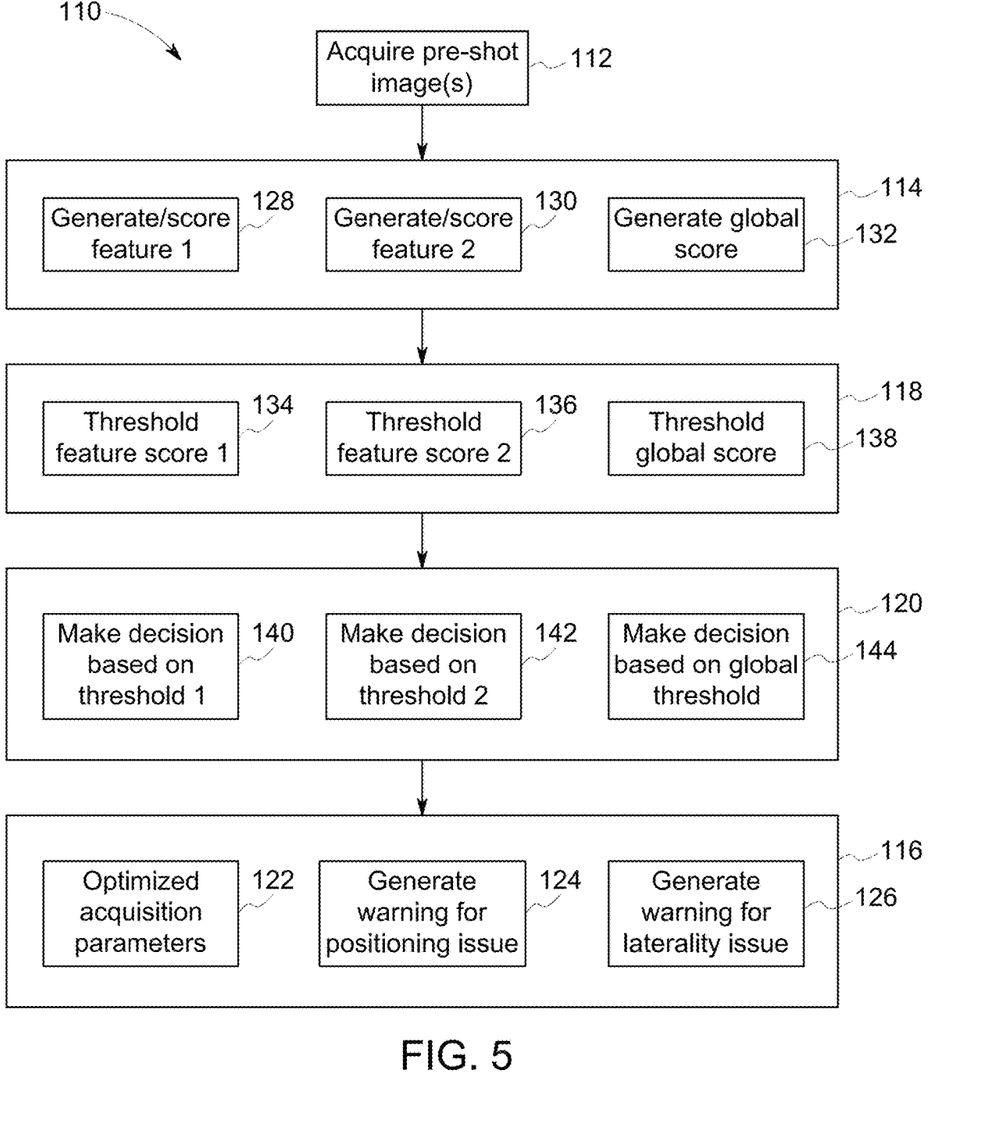
FIG. 5 is a flow chart of another embodiment of the method for imaging an object via pre-shot processing of FIG. 2, in accordance with an embodiment of the present invention.

Moving to FIG. 5, another embodiment of the method 110 for imaging the object 12 via pre-shot processing is shown. The method 110 include acquiring 112 one or more pre-shot images, generating/scoring 114 one or more features, e.g., feature maps, from the one or more pre-shot images, and performing 116 an action based at least in part on the generated/scored features. In embodiments, the method 110 may further include thresholding 118 the generated/scored features and making decisions 120 as to which action should be performed 116.

In embodiments, the performed actions 116 may include optimizing 122 one or more acquisition parameters used to acquire 24 the diagnostic images, generating 124 a warning that the position of the object 12 is not acceptable, and/or generating 126 a warning that the matched anatomical symmetry of the object 12 is not acceptable. For example, in embodiments, one of the generated/scored features, e.g., 130, may be attenuation of the radiation rays/photons across the object 12, i.e., controller 16 may determine the most attenuating region of the object 12 in order to determine the optimal power parameters, e.g., kVp and/or mAs, and/or x-ray tube anode and filter materials, of the imaging device 14 for acquiring 24 the diagnostic images, which in turn, may provide for improved signal to noise ratios.

Further, while FIG. 5 depicts the generation of the warnings for object position 124 and matched anatomical symmetry 126 as separate warnings, it is to be understood that, in embodiments, the warnings 124 and 126 may be combined into a single warning. In other words, matching an anatomical symmetry to the object 12 may from part of the generated/scored positional feature/map of the object 12.

In embodiments, generating/scoring 114 the feature/maps may include generating/scoring 128, 130 individual feature/maps. In embodiments, the individually generated/scored feature/maps, e.g., 128 and 130 may be combined/aggregated into a global score 132, e.g., via summing weighted values of the individually generated/scored feature/maps 128 and/or 130. As will be understood, however, other embodiments may utilize other methods of aggregating the individual generated/scored feature/maps 128 and/or 130, e.g., averaging.

In embodiments, thresholding 118 the generated/scored feature/maps may include thresholding 134 and/or 136 individual scored feature/maps and/or thresholding 138 a global score. For example, the global score generated at step 132 may be thresholded at step 138. In embodiments, thresholding 134, 136, and/or 138 may involve testing the corresponding feature/map/global scores to see if they exceed a particular value, and if so, triggering/preforming 116 one or more of the actions.

In embodiments, deciding 120 which actions should be performed 116 may include deciding 140 and 142 based on individual thresholded results, e.g., 134 and 136, and/or deciding 144 based on a global thresholded result, e.g., 138. The decisions may include determining if the object 12 needs to be repositioned, determining if one or more acquisition parameters needs to be adjusted, and/or determining if the matched symmetry/laterality of the object 12 is acceptable/expected.

Figure 6:
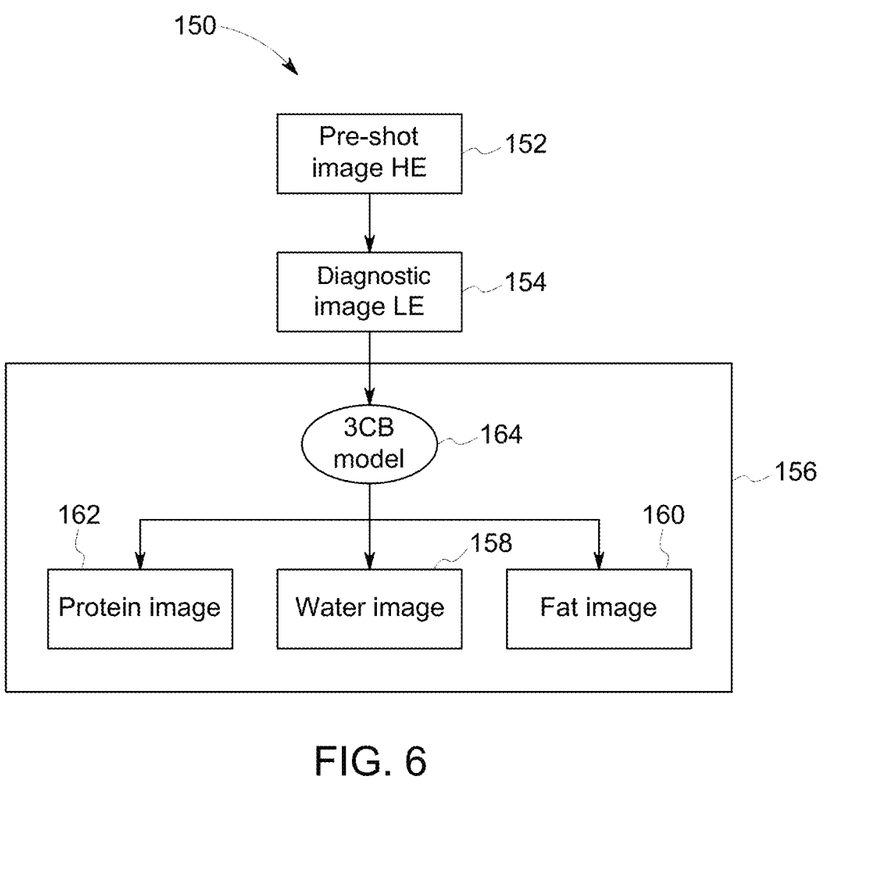
FIG. 6 is a flow chart of yet another embodiment of the method for imaging an object via pre-shot processing of FIG. 2, in accordance with an embodiment of the present invention.

Illustrated in FIG. 6 is yet another embodiment of the method 150 for imaging an object 12 via pre-shot processing. The method 150 includes acquiring 152 at least one pre-shot image using a first energy spectrum; acquiring 154 one or more diagnostic images via a second energy spectrum lower than the first energy spectrum; and/or generating 156 a material-equivalent image, e.g., a water image, a fat image, and/or a protein image, based at least in part on the one or more pre-shot images and the diagnostic images. For example, in embodiments, the material-equivalent image may be a water-equivalent image 158, a fat-equivalent image 160, and/or a protein-equivalent image 162. The first energy spectrum used to acquire 152 the one or more pre-shot images may be between about thirty-five (35) keV to about fifty (50) keV, and the second energy spectrum used to acquire 154 the one or more diagnostic images may be between about ten (10) keV to about thirty-five (35) keV.

In embodiments, generation 156 of the material-equivalent image may be based at least in part on a 3CB decomposition algorithm/model 164. In embodiments, the 3CB model 164 may be applied to both the acquired 152 high-energy pre-shot images and the acquired 154 low-energy diagnostic images.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for imaging an object via pre-shot processing is provided. The system includes an imaging device operative to image the object, and a controller in electronic communication with the imaging device. The controller is operative to acquire at least one pre-shot image of the object via the imaging device; and to generate, based at least in part on the at least one pre-shot image, an indicator that corresponds to the likelihood that one or more diagnostic images of the object acquired via the imaging device will be medically deficient. In certain embodiments, the controller is further operative to generate a global score derived from one or more features of the at least one pre-shot image. In such embodiments, the indicator is based at least in part on the global score. In certain embodiments, the controller is further operative to restrict imaging of the object via the imaging device if the global score does not exceed a threshold. In certain embodiments, the one or more features include at least one of a density of the object, a masking effect of the object, and a position of the object. In certain embodiments, the object is a human breast, the one or more features includes the position of the breast, and the global score is based at least in part on at least one of an inframammary fold of the breast, a nipple of the breast, and a pectoral muscle associated with the breast. In certain embodiments, the controller is further operative to match an anatomical symmetry to the object. In such embodiments, the indicator is based at least in part on the matched anatomical symmetry. In certain embodiments, the controller is further operative to restrict imaging of the object via the imaging device when the matched anatomical symmetry of the object is not an expected anatomical symmetry for the object. In certain embodiments, the controller generates the indicator based at least in part on a machine learning model. In certain embodiments, the controller is further operative to acquire the at least one pre-shot image using a first energy spectrum, and to acquire the one or more diagnostic images using a second energy spectrum lower than the first energy spectrum. In such embodiments, the controller is further operative to generate a material-equivalent image based at least in part on the at least one pre-shot image and the one or more diagnostic images.

Other embodiments provide for a method for imaging an object via pre-shot processing. The method includes acquiring at least one pre-shot image of the object via an imaging device. The method further includes generating, via a controller and based at least in part on the at least one pre-shot image, an indicator that corresponds to the likelihood that one or more diagnostic images of the object acquired via the imaging device will be medically deficient. In certain embodiments, the method further includes generating, via the controller, a global score derived from one or more features of the at least one pre-shot image. In such embodiments, the indicator is based at least in part on the global score. In certain embodiments, the method further includes restricting, via the controller, imaging of the object with the imaging device if the global score does not exceed a threshold. In certain embodiments, the one or more features include at least one of a density of the object, a masking effect of the object, and a position of the object. In certain embodiments, the object is a human breast, the one or more features includes the position of the breast, and the global score is based at least in part on at least one of an inframammary fold of the breast, a nipple of the breast, and a pectoral muscle associated with the breast. In certain embodiments, the method further includes matching, via the controller, an anatomical symmetry to the object. In such embodiments, the indicator is based at least in part on the matched anatomical symmetry. In certain embodiments, the method further includes restricting, via the controller, imaging of the object with the imaging device when the matched anatomical symmetry of the object is not an expected anatomical symmetry for the object. In certain embodiments, the controller generates the indicator based at least in part on a machine learning model. In certain embodiments, the method further includes acquiring one or more diagnostic images via the imaging device and generating, via the controller, a material-equivalent image based at least in part on the at least one pre-shot image and the one or more diagnostic images. In such embodiments, the at least one pre-shot image is acquired with a first energy spectrum and the one or more diagnostic images are acquired with a second energy spectrum lower than the first energy spectrum.

Yet still other embodiments provide for a non-transitory computer readable medium storing instructions. The stored instructions adapt a controller to acquire at least one pre-shot image of an object via an imaging device. The stored instructions further adapt the controller to generate, based at least in part on the at least one pre-shot image, an indicator that corresponds to the likelihood that one or more diagnostic images of the object acquired via the imaging device will be medically deficient.

Yet still other embodiments provide for a system for imaging an object via pre-shot processing. The system includes an imaging device operative to image the object, and a controller in electronic communication with the imaging device. The controller is operative to acquire the at least one pre-shot image using a first energy spectrum, and to acquire one or more diagnostic images via the imaging device using a second energy spectrum lower than the first energy spectrum. The controller is further operative to generate a material-equivalent image based at least in part on the at least one pre-shot image and the one or more diagnostic images. In certain embodiments, the controller is further operative to generate, based at least in part on the at least one pre-shot image, an indicator that corresponds to the likelihood that the one or more diagnostic images will be medically deficient.

Yet still other embodiments provide for a non-transitory computer readable medium storing instructions. The stored instructions adapt a controller to acquire at least one pre-shot image via an imaging device using a first energy spectrum; and to acquire one or more diagnostic images via the imaging device using a second energy spectrum lower than the first energy spectrum. The stored instructions further adapt the controller to generate a material-equivalent image based at least in part on the at least one pre-shot image and the one or more diagnostic images.

Accordingly, as will be appreciated, by taking advantage of the information available within a pre-shot image, some embodiments of the present invention provide for improved prediction/calculation as to the acceptability of subsequent diagnostic images, prior to their acquisition, so as to reduce the number of unacceptable diagnostic images, which in turn, may reduce the amount of unnecessary radiation exposure to a patient.

Further, by utilizing a machine learning model to access/analyze the pre-shot images, as opposed to relying on human analysis and/or more rigid computerized approaches, some embodiments of the present invention provide for improved detection and/or correction of possible problems/issues with an object to be imaged, prior to the acquisition of diagnostic images, as compared to systems and methods that rely substantially on human assessment/analysis of a pre-shot image.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for imaging an object via pre-shot processing, the system comprising:
   an imaging device operative to image the object;
   a controller in electronic communication with the imaging device and operative to:
      acquire at least one pre-shot image of the object via the imaging device;
      generate, based at least in part on the at least one pre-shot image, an indicator that corresponds to a likelihood that one or more subsequent diagnostic images of the object acquired via the imaging device will be medically deficient; and
      generate a global score derived from one or more features of the at least one pre-shot image,
      wherein the indicator is based at least in part on the global score.

2. The system of claim 1 wherein the controller is further operative to:
   restrict imaging of the object via the imaging device if the global score does not exceed a threshold.

3. The system of claim 1, wherein the one or more features include at least one of a density of the object, a masking effect of the object, and a position of the object.

4. The system of claim 3, wherein the object is a human breast, the one or more features includes the position of the breast, and the global score is based at least in part on at least one of an inframammary fold of the breast, a nipple of the breast, and a pectoral muscle associated with the breast.

5. The system of claim 1, wherein the controller is further operative to:
   match an anatomical symmetry to the object,
   wherein the indicator is based at least in part on the matched anatomical symmetry.

6. The system of claim 5, wherein the controller is further operative to:
   restrict imaging of the object via the imaging device when the matched anatomical symmetry of the object is not an expected anatomical symmetry for the object.

7. The system of claim 1, wherein the controller generates the indicator based at least in part on a machine learning model.

8. The system of claim 1, wherein the controller is further operative to:
   acquire the at least one pre-shot image using a first energy spectrum;
   acquire the one or more diagnostic images using a second energy spectrum lower than the first energy spectrum; and
   generate a material-equivalent image based at least in part on the at least one pre-shot image and the one or more diagnostic images.

9. A method for imaging an object via pre-shot processing, the method comprising:
   acquiring at least one pre-shot image of the object via an imaging device;

generating, via a controller and based at least in part on the at least one pre-shot image, an indicator that corresponds to a likelihood that one or more subsequent diagnostic images of the object acquired via the imaging device will be medically deficient; and generating, via the controller, a global score derived from one or more features of the at least one pre-shot image, wherein the indicator is based at least in part on the global score.

10. The method of claim 9 further comprising:

restricting, via the controller, imaging of the object with the imaging device if the global score does not exceed a threshold.

11. The method of claim 9, wherein the one or more features include at least one of a density of the object, a masking effect of the object, and a position of the object.

12. The method of claim 11, wherein the object is a human breast, the one or more features includes the position of the breast, and the global score is based at least in part on at least one of an inframammary fold of the breast, a nipple of the breast, and a pectoral muscle associated with the breast.

13. The method of claim 9 further comprising:

matching, via the controller, an anatomical symmetry to the object, wherein the indicator is based at least in part on the matched anatomical symmetry.

14. The method of claim 13 further comprising:

restricting, via the controller, imaging of the object with the imaging device when the matched anatomical symmetry of the object is not an expected anatomical symmetry for the object.

15. The method of claim 9, wherein the controller generates the indicator based at least in part on a machine learning model.

16. The method of claim 9 further comprising:

acquiring one or more diagnostic images via the imaging device;

generating, via the controller, a material-equivalent image based at least in part on the at least one pre-shot image and the one or more diagnostic images; and wherein the at least one pre-shot image is acquired with a first energy spectrum and the one or more diagnostic images are acquired with a second energy spectrum lower than the first energy spectrum.

17. A non-transitory computer readable medium storing instructions that adapt a controller to:

acquire at least one pre-shot image of an object via an imaging device;

generate, based at least in part on the at least one pre-shot image, an indicator that corresponds to the likelihood that one or more subsequent diagnostic images of the object acquired via the imaging device will be medically deficient; and generate a global score derived from one or more features of the at least one pre-shot image, wherein the indicator is based at least in part on the global score.

18. A system for imaging an object via pre-shot processing, the system comprising:

an imaging device operative to image the object;

a controller in electronic communication with the imaging device and operative to:

acquire the at least one pre-shot image using a first energy spectrum;

acquire one or more subsequent diagnostic images via the imaging device using a second energy spectrum lower than the first energy spectrum;

generate a material-equivalent image based at least in part on the at least one pre-shot image and the one or more subsequent diagnostic images; and generate, based at least in part on the at least one pre-shot image, an indicator that corresponds to a likelihood that one or more diagnostic images of the object acquired via the imaging device will be medically deficient.

19. A non-transitory computer readable medium storing instructions that adapt a controller to:

acquire at least one pre-shot image via an imaging device using a first energy spectrum;

acquire one or more subsequent diagnostic images via the imaging device using a second energy spectrum lower than the first energy spectrum;

generate a material-equivalent image based at least in part on the at least one pre-shot image and the one or more subsequent diagnostic images; and generate, based at least in part on the at least one pre-shot image, an indicator that corresponds to a likelihood that one or more diagnostic images of the object acquired via the imaging device will be medically deficient.

* * * * *